(12) United States Patent  (10) Patent No.: US 8,318,107 B2
Rieder et al.  (45) Date of Patent: Nov. 27, 2012

(54) APPARATUS AND METHOD FOR SPECIMEN SUITABILITY TESTING

(75) Inventors: Ronald J. Rieder, Medford, MA (US); John R. Howatt, Bedford, MA (US); Alexander Sloutsky, Newton, MA (US); John Oleksy, Sudbury, MA (US)

(73) Assignee: Biosense Technologies, Inc., Woburn, MA (US)

( * ) Notice: Subject to any disclaimer, the term of this patent is extended or adjusted under 35 U.S.C. 154(b) by 128 days.

(21) Appl. No.: 12/733,519

(22) PCT Filed: Aug. 29, 2008

(86) PCT No.: PCT/US2008/010247
§ 371 (c)(1),
(2), (4) Date: Mar. 5, 2010

(87) PCT Pub. No.: WO2009/032309
PCT Pub. Date: Mar. 12, 2009

(65) Prior Publication Data
US 2011/0135540 A1  Jun. 9, 2011

Related U.S. Application Data

(60) Provisional application No. 60/967,496, filed on Sep. 5, 2007.

(51) Int. Cl.
*G01N 33/00* (2006.01)

(52) U.S. Cl. ............... 422/404; 422/68.1; 422/82.01
(58) Field of Classification Search ............... 422/68.1, 422/82.01, 404
See application file for complete search history.

(56) References Cited

U.S. PATENT DOCUMENTS
2003/0064422 A1* 4/2003 McDevitt et al. ............ 435/7.32
* cited by examiner

*Primary Examiner* — Sam P Siefke
(74) *Attorney, Agent, or Firm* — Arendt & Associates IP Group; Jacqueline Arendt

(57) ABSTRACT

Disclosed herein are a system for collecting a sample and optionally detecting or analyzing an electrical property thereof, the method comprising: means for obtaining a sample in a sample container; means for directing the sample into a sensing chamber in fluid communication with the sample container, the sensing chamber comprising a plurality of sensing chamber electrodes positioned at the sensing chamber and configured to be in contact with the sample when the sample is directed into the sensing chamber; means for applying an electrical signal to the sample with a read-out analyzer via the plurality of sensing chamber electrodes; the plurality of sensing chamber electrodes in operable communication with the read-out analyzer; and means for detecting the effect of the sample on the electrical signal, thereby determining an electrical property of the sample.

20 Claims, 7 Drawing Sheets

APPARATUS AND METHOD FOR SPECIMEN SUITABILITY TESTING

RELATED APPLICATION

This application claims the benefit of U.S. Provisional Application No. 60/967,496 filed on 5 Sep. 2007, the teachings of which are incorporated by reference herein in their entirety.

BACKGROUND OF THE INVENTION

Two billion persons, or about one third of the world's population, are estimated to be infected with the bacterium that causes tuberculosis (TB), a highly contagious disease that is one of the world's leading infectious causes of death. Between the years 2000 and 2020, it is estimated that one billion new TB infections will occur, resulting in 200 million people becoming sick and at least 35 million deaths (1).

Under the World Health Organization's (WHO's) current global TB control guidelines, smear microscopy testing of sputum samples of individuals exhibiting symptoms of the disease is used to identify patients as positive for acid-fast bacilli (AFB). If an individual tests positive for AFB, s/he meets the inclusion criteria for enrollment into WHO's "Direct Observation of Therapy Program" (DOTS). However, the reliability of smear microscopy test results, and other test modalities, depends on initially having good quality diagnostic samples on which to perform the test. A good quality sample is one containing an amount of sputum sufficient to detect the causative pathogen. Poor quality samples can directly impact the availability of WHO treatment protocol. A false-negative test result leads to denied treatment, and consequently, to the further spread of the disease.

The current case detection rate was most recently stated in the literature as 53 percent (2). A significant percentage of the missing cases may be due to false negative diagnoses resulting from testing specimens having amounts of sputum that are actually inadequate for such testing. Typically, a sputum sample is collected by means of the individual deeply inhaling and exhaling repeatedly, followed by coughing from as deep inside the chest as possible, thereby expectorating from the lungs or pulmonary passageways, into a collection container. However, often what is collected is mostly saliva, and the sample contains little or no real sputum. Although sputum can be thick and mucoid, it can also be fluid and similar in appearance to saliva. Thus, it is difficult to ascertain visually, at the time of collection, whether or not a collected sample is of sufficient quality, i.e., containing sufficient sputum, for AFB smear microscopy testing.

If a collected sample has an insufficient sputum concentration, it can yield a false-negative test result, and the patient would not be treated, and possibly would not be further observed. The patient may find it difficult to travel again to a medical center, and diagnosis may be delayed.

According to a 2003 epidemiological study (3) of TB, adverse outcomes of delay in initiating medical treatment include increased probability of death (4), increased risk of transmission to health care workers and others if the patient is hospitalized and not isolated (5), and increased transmission within the community (3).

In order to accurately diagnose TB, and promptly initiate both medical treatment and a rapid public health response, a test specimen of good quality must first be obtained from the individual. Currently, however, there is no practical method or device available, prior to laboratory testing for TB, to distinguish between usable sputum specimens and sub-standard specimens which are a source for false-negative AFB results. Clinical studies by Sloutsky (6) and others have shown that up to one-quarter or more of all TB sputum specimens collected may have limited diagnostic value because of the absence of adequate amounts of sputum in the sample, and that improvement in specimen quality can result in increased detection by as much as tens of percent (7).

Thus, there is an on-going clinical need for an improved method and apparatus to quickly identify, at the time a specimen is obtained from an individual, the suitability of the specimen for AFB smear microscopy testing. If such improved testing is available at the time of collection of a sample, a patient can be asked to remain long enough for the quality of the sample to be ascertained. If the sample is found to be unsuitable, the patient can provide another sample soon after.

There exists a need for an apparatus and a method of assessing specimen quality at the point of collection in order to enable the clinician to identify poor quality specimens and avoid submitting such specimens for diagnostic testing. Clinicians would be enabled to initially obtain better quality specimens, and to thereby maximize the rate of TB detection.

Another currently unmet need is a method of standardizing the diagnostic quality of clinical tuberculosis specimens. Yet another need is for a specimen collection and analysis device that can be conveniently handled so as to minimize the spread of infection during and subsequent to the specimen collection procedure.

SUMMARY OF THE INVENTION

Disclosed herein are a device and method that provide for such improvements. The invention inter alia includes the following, alone or in combination. An embodiment of the present invention relates to an apparatus and method for collecting a sample and optionally detecting or analyzing an electrical or magnetic property of the sample.

One embodiment of the invention is an apparatus for collecting a sample and optionally detecting or analyzing an electrical or magnetic property thereof, the apparatus comprising: a sample container for initially receiving the sample, the sample container comprising an outer surface and an inner surface, an open top end, and a closed bottom end; a hollow piston having a hollow piston inner surface and a hollow piston outer surface, the hollow piston shaped to be slidably disposed within the sample container, and to operate substantially coaxially within the sample container to sweep the sample to the bottom end of the sample container, the hollow piston having a hollow piston inlet port and a hollow piston outlet port; a sensing chamber positioned within the hollow piston, the sensing chamber having a sensing chamber inlet port in fluid communication with the hollow piston outlet port, so that as the hollow piston operates to sweep the sample to the bottom end of the sample container, the sample is directed out of the sample container, through the hollow piston inlet port, through the hollow piston, out the hollow piston outlet port and through the sensing chamber inlet port into the sensing chamber, thereby filling a volume within the sensing chamber with a portion of the sample; and a plurality of sensing chamber electrodes at the sensing chamber, the plurality of sensing chamber electrodes configured to contact the portion of the sample contained in the sensing chamber.

Another embodiment is an apparatus for collecting a sample and optionally detecting or analyzing an electrical property thereof, the apparatus comprising: a sample container for initially receiving a sample; a syringe mounted on a support, the syringe comprising a syringe plunger; a trigger or lever attached to the support and mechanically connected to the syringe plunger for drawing in or for expelling the sample; a sensing chamber comprising a plurality of sensing chamber electrodes, the sensing chamber fluidly connected to the sample container and positioned between the sample container and the syringe, such that when the trigger or lever is activated for drawing in the sample, the sample is drawn into the sensing chamber and placed in contact with the plurality of sensing chamber electrodes;

a plurality of sensing chamber contacts disposed external to the sensing chamber, and operably connected in conductive communication with the sensing chamber electrodes; and a read-out analyzer including a plurality of mating contacts configured to mate with the plurality of sensing chamber contacts, the read-out analyzer configured for detecting and analyzing a property of the sample, and the plurality of mating contacts of the read-out analyzer configured to interface with the sensing chamber contacts, thereby enabling application of an electrical signal to the sample for detection and analysis.

In another aspect, the invention relates to a method of reducing a volume of a sample and optionally detecting and analyzing an electrical property of the sample, the method comprising: directing a sample into a sensing chamber, the sensing chamber comprising a plurality of sensing chamber electrodes positioned within the sensing chamber and configured to be in contact with the sample when the sample is directed into the sensing chamber; applying an electrical signal to the sample with a read-out analyzer via the plurality of sensing chamber electrodes; the plurality of sensing chamber electrodes in operable communication with the read-out analyzer; and detecting the effect of the sample on the electrical signal, thereby determining an electrical property of the sample.

Yet another embodiment of the invention is a system for collecting a sample and optionally detecting or analyzing an electrical property thereof, the method comprising: means for obtaining a sample in a sample container; means for directing the sample into a sensing chamber in fluid communication with the sample container, the sensing chamber comprising a plurality of sensing chamber electrodes positioned at the sensing chamber and configured to be in contact with the sample when the sample is directed into the sensing chamber; means for applying an electrical signal to the sample with a read-out analyzer via the plurality of sensing chamber electrodes; the plurality of sensing chamber electrodes in operable communication with the read-out analyzer; and means for detecting the effect of the sample on the electrical signal, thereby determining an electrical property of the sample.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles & char of the various embodiments of invention.

DETAILED DESCRIPTION OF THE INVENTION

Figure 1:
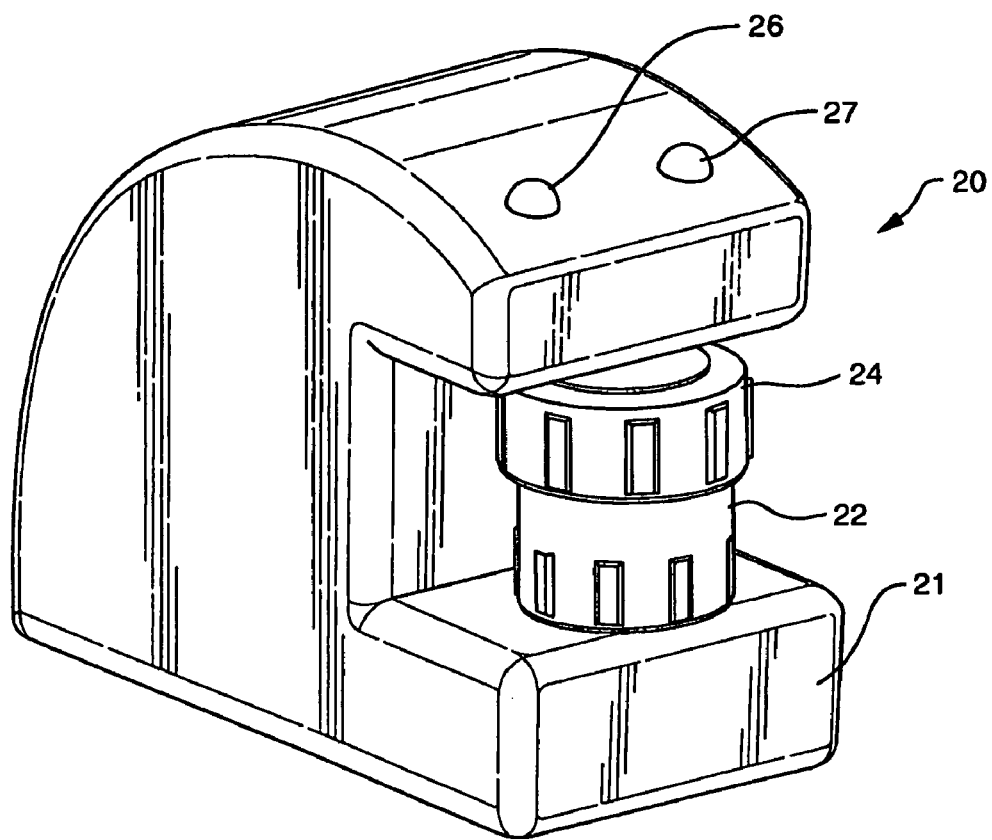
FIG. 1 is a perspective view of a disposable self-contained specimen cup along with a corresponding read-out analyzer according to an embodiment of the invention.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Disclosed herein is a system including an apparatus and method for collecting and optionally analyzing a sample. Advantageously, the invention addresses a critical and heretofore unmet clinical need: the capability of initially, at the point of collection, distinguishing between usable and substandard TB specimens prior to time-consuming laboratory procedures such as gram-staining and culture.

The improvements disclosed herein, by reducing the time needed to determine whether or not a specimen collected from an individual is suitable for AFB smear microscopy testing, are likely to also shorten the time elapsed before treatment of the patient is begun, thereby lessening the clinical deterioration of the patient and lessening the risk of transmission of TB in the community.

The disclosed system may be used further to establish a clinical standard for the diagnostic quality of clinical tuberculosis specimens. An embodiment of the invention is a non-invasive specimen collection and analysis system capable of identifying poor quality TB specimens in real-time at the point of collection. Advantageously, the sensing process of an exemplary embodiment exploits electrical differences between a sample of saliva and a sample of sputum. These differences are related to differences in the content of DNA and other highly charged molecules in saliva and sputum and are determined by monitoring and analyzing the capacitance of a sample and comparing it to that of a standard.

The present invention relates to methods and compositions for collecting and directing a sample into a sensing chamber, and rapidly detecting and analyzing an electrical property or an optical property of the sample. An apparatus and a method according to embodiments of the invention may be used to collect and analyze many different types of samples, for example, a fluid or a gel. Non-limiting examples of such samples include biological specimens such as sputum, blood, urine, and cells that have been homogenized in a blender.

As used herein, the term "detecting" refers to either identification or quantification of an electrical property or an optical property of the sample collected. "Detecting" is intended to include determining the presence or absence of a property or quantifying the magnitude or amount of a property. The term "detecting" thus refers to the use of the compositions and methods of the present invention for qualitative and quantitative determinations.

Disclosed herein is a system for collecting a sample and optionally detecting or analyzing an electrical property thereof, the method comprising: means for obtaining a sample in a sample container; means for directing the sample into a sensing chamber in fluid communication with the sample container, the sensing chamber comprising a plurality of sensing chamber electrodes positioned at the sensing chamber and configured to be in contact with the sample when the sample is directed into the sensing chamber; means for applying an electrical signal to the sample with a read-out analyzer via the plurality of sensing chamber electrodes; the plurality of sensing chamber electrodes in operable communication with the read-out analyzer; and means for detecting the effect of the sample on the electrical signal, thereby determining an electrical property of the sample.

Figure 2A:
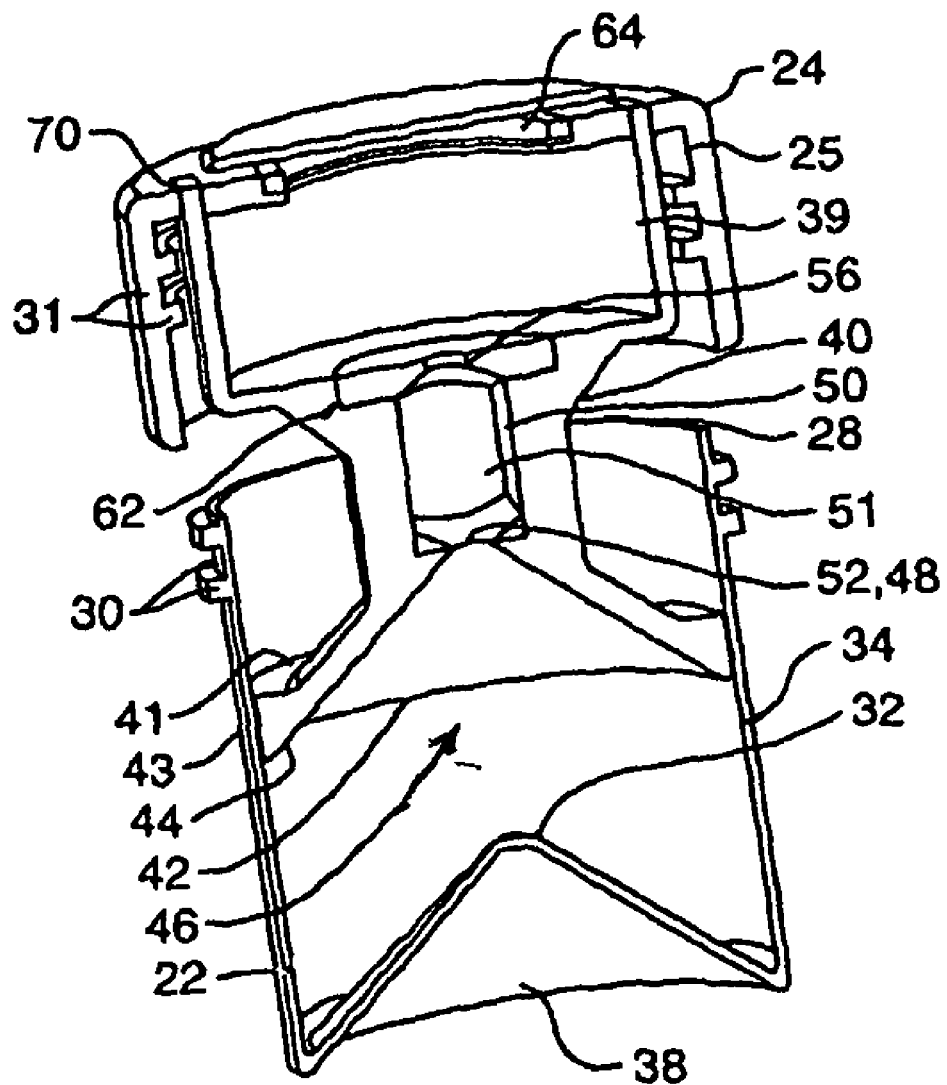
FIG. 2A is a partial cutaway, side elevation view of the cap, hollow piston and sample container according to an embodiment of the invention.

Turning now to the drawings, FIG. 1 depicts an over-all arrangement, according to an embodiment of the invention, of a read-out analyzer (20) having a support base (21) for holding a preferably disposable self-contained sample container (22) for holding a sample with a vented cap (24). As the terms are used herein, "sample" and "specimen" have the same meaning and are used interchangeably. Further, the terms "container", "cup", and "vessel", have the same meaning and are also used interchangeably. The terms "hollow piston" and "plunger" are also used interchangeably. As shown in FIG. 2A, within the sample cup (22), a vented cap (24) and a plunger (40) mechanism operate to sweep the sample toward the bottom end of the vessel or sample container (22) and direct the sample out of the sample container (22), through the hollow piston inlet port (46), through the hollow piston (40), out the hollow piston outlet port (48) and through the sensing chamber inlet port (52) into the sensing chamber (50). In this manner a volume within the sensing chamber (50) is filled with a portion of the sample. A plurality of sensing chamber electrodes (51) at the sensing chamber (50) is configured to contact the portion of the sample contained in the sensing chamber (50).

The sample cup (22) is then inserted into the read-out instrument or analyzer (20) that is used to measure the corresponding impedance and to compare it with a predetermined threshold associated with an acceptable sample. In the embodiment shown in FIG. 1, annunciators are employed to indicate the state of the sample measured. On the apparatus, the annunciator may be a colored light that is illuminated in real-time, indicating the quality of the sample. For example, illumination of a green light (26) indicates that the sample is of acceptable quality for further testing. Illumination of a red light (27) indicates that the sample is unacceptable. Advantageously, the real-time speedy determination of sample quality may be done while a patient waits. If a re-test is needed, the patient may readily submit another sample and wait again for a determination. The disclosed invention minimizes the need for a patient to leave the test site and return at a later date due to false or uncertain results. It also minimizes the chance that a patient with a communicable disease such as, for example, tuberculosis, will return untreated to his workplace or community to potentially spread the disease during a period of time that would traditionally be needed for analysis of a specimen without the use of the disclosed device for determining specimen quality.

It should be appreciated that as used herein, the sample may comprise a biological specimen, or a non-biological specimen, and may include a fluid or a gel.

The disclosed apparatus may include electrical control circuitry supporting output signaling chosen from at least one of: optical read-out capability, auditory signaling, and mechanical signaling, such output signaling used to indicate either an acceptable or a non-acceptable quality of the sample.

The Sample Container

As shown in FIG. 2A, in one embodiment of the invention the sample container (22) has an open top end (28) for initially receiving a sample, a closed bottom end (38), an outer surface, and an interior surface (34). In the embodiment shown in FIG. 2A, the bottom interior surface (32) of the sample container (22) may have a substantially conical or frusto-conical shape, which shape tends to direct the sample up into the hollow piston inlet port (46) as the hollow piston (40) is lowered into the sample container (22). The interior surface (34) of the sample container (22) may be any one of a variety of shapes, provided that the shape is complementary to the shape of the bottom portion (42) of the hollow piston (40), and provided that the shape serves to direct the specimen toward the smaller volume of the sensing chamber (50). One embodiment may be a square or peg-shaped sample container (22) that includes a conical interior geometry that serves to, upon lowering the hollow piston (40) into the sample container (22), direct the sample into the sensing chamber (50). The term "conical", when used with reference to the sample container (22) and the hollow piston (40), includes both solid conical shapes as well as infundibular, that is, hollow funnel shapes. By "substantially conical shape" is meant that there is no true apex, but instead the cone may be a frustum having a pseudo-apex. A frusto-conical shape is the shape of a cone intersected by a plane that cuts off the actual apex of the cone.

In various embodiments of the invention the overall size of the sample container may be varied. For example, a larger sized container may make the cup easier to hold and manipulate, and allow for a larger overflow volume to accommodate large volume specimens. Size changes will not affect the current performance of the device.

The sample container (22) may be a centrifugable tube and/or may be capable of withstanding gamma-irradiation without breakdown of its composition.

The Analyzer

As shown in FIG. 1 disclosed herein is an analyzer (20) including a support comprising a base (21) upon which the closed bottom end of the sample container (22) may be positioned, at least one mating contact oriented and positioned to contact the at least one contact (70) at the hollow piston outer surface or the outer surface of the vented cap (24) when the sample container (22) with the vented cap (24) mated thereon is positioned on the support base (21); and the read-out analyzer (20) in electrical contact with the at least one mating contact (70).

The disclosed apparatus may further comprise electrical control circuitry supporting output signaling chosen from at least one of: optical read-out capability, auditory signaling, and mechanical signaling, such output signaling used to indicate either an acceptable or a non-acceptable quality of the sample. The read-out analyzer (20) may further include data storage hardware or media and software to record sample readings for future analysis.

The Hollow Piston in Relation to the Sample Container.

The hollow piston (40) is shaped to be slidably disposed within the sample container (22), and to operate substantially coaxially within the sample container (22). In the embodiment shown in FIG. 2, the hollow piston (40) has a bottom portion (42) having an inner surface that is shaped similar to an inverted funnel or cone, the inner surface substantially complementary with respect to the inner surface (32) of the closed bottom end (38) of the sample container (22). Because these two surfaces are substantially complementary to one another, when the hollow piston (40) is lowered into the sample container (22), the hollow piston (40) can sweep the sample to the bottom end of the sample container (22); and the inner surface (44) of the conical bottom portion (42) of the hollow piston (40) matingly engages with the inner surface (32) of the closed bottom end (38) of the sample container (22).

The hollow piston (40) includes a bottom piston inlet port (46) and a hollow piston outlet port (48); a sensing chamber (50) positioned within the hollow piston (40), the sensing chamber (50) having a sensing chamber inlet port (52) in fluid communication with the hollow piston outlet port (48), so that as the hollow piston (40) operates to sweep the sample to the bottom end of the sample container (22), the sample is directed out of the sample container (22), through the bottom piston inlet port (46), through the hollow piston (40), out the hollow piston outlet port (48) and through the sensing chamber inlet port (52) into the sensing chamber (50, thereby filling a volume within the sensing chamber (50) with a portion of the sample. In one embodiment, the hollow piston outlet port (48) and the sensing chamber inlet port (52) are adjacent or adjoining to one another.

The sliding of the hollow piston (40) into the sample container (22) exerts a downward pressure on the sample, and tends to draw the sample together as the concave inner surface of the conical bottom portion (42) of the hollow piston (40) moves closer to the convex closed bottom end (38) of the sample container (22), and to drive the sample through the hollow piston inlet port (46) and out the hollow piston outlet port (48).

The various sections or parts of the hollow piston (40) may be "integral to" each other, or the parts may be attached to each other. By "integral to" is meant that the sections of the piston are manufactured as a single piece. For example, the piston may be formed as a single piece by injection molding from high density polyethylene. The sections of the piston are attached to each other if the two sections are manufactured as separate pieces.

In the embodiment shown in FIG. 2A, the closed bottom end (38) of the sample container (22) exhibits a substantially convex inner surface (32), and the hollow piston (40) exhibits a bottom portion (42) having a substantially concave inner surface substantially complementary with respect to the convex inner surface of the closed bottom end (38) of the sample container (22). As shown in FIG. 2A, the closed bottom end (38) of the sample container (22) has an inner surface (32) which is substantially frustoconical in shape.

In yet another embodiment of the invention, both the bottom portion (42) of the hollow piston (40) and the closed bottom end (38) of the sample container (22) are at least one of substantially flat, angled, conical, frustoconical, pyramidal, frustopyramidal, and hemispherical. With no more than routine experimentation, the hollow piston (40) and the closed bottom end (38) of the sample container (22) may be constructed such that they may have any shapes that are substantially complementary to one another. The best shape for a particular use may be determined by the viscosity of the sample or the volume of the sample.

In the embodiment shown in FIG. 2A, a bottom portion (42) of the hollow piston (40) comprises an external circumferential flange (41) substantially at the bottom piston inlet port (46). The external circumferential flange (41) provides an increased area of contact with the inner surface of the sample container (22) and facilitates the sweeping of the sample off the inner surface of the sample container (22).

Figure 2B:
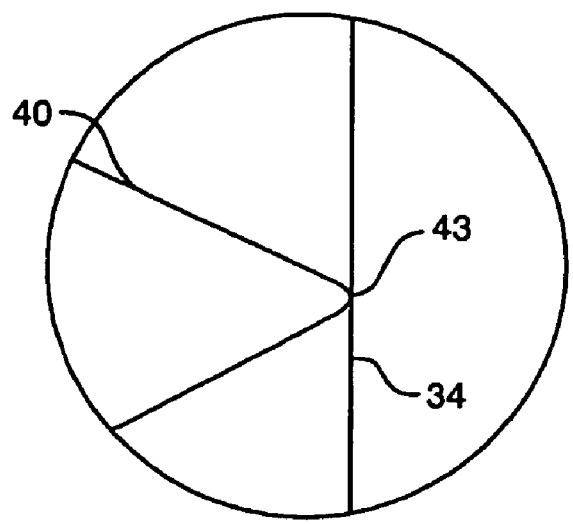
FIG. 2B is a schematic representation of the point contact of a hollow piston and the interior surface of a container wall, wherein the bottom circumferential edge of the hollow piston is rounded.

FIG. 2B schematically depicts an embodiment of the hollow piston (40) wherein the external circumferential flange (41) is reduced to a point, and wherein such a point contact with the inner surface (34) of a wall of the sample container (22) would provide minimal surface area for sweeping the sample off of the inner surface (34) of the sample container (22) wall.

Figure 2C:
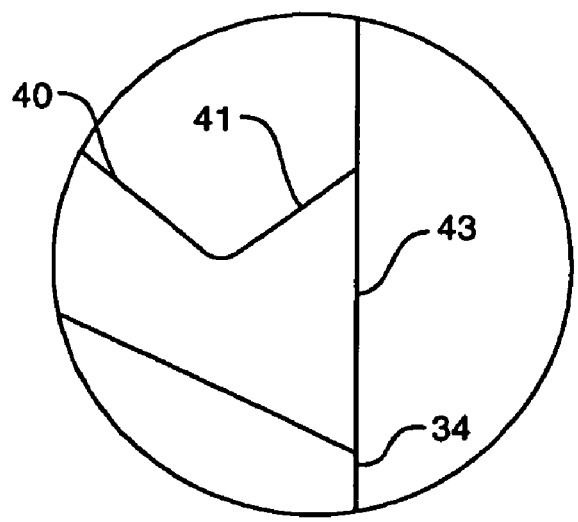
FIG. 2C is a schematic representation of the area of contact of a hollow piston with the interior surface of a container wall, wherein the bottom circumferential edge of the hollow piston is flanged, thereby increasing the area of contact relative to that shown in FIG. 2B.

In a preferred embodiment of the piston depicted schematically in FIG. 2C, and in FIG. 2A, the shape of the external circumferential flange (41) of the hollow piston (40) provides an increased area of contact (43) of the hollow piston (40) with the inner surface (34) of the sample container (22). The increased area of contact (43) facilitates the sweeping of the sample off the inner surface (34) of the sample container (22).

The Overflow Chamber and the Vented Cap

Figure 3:
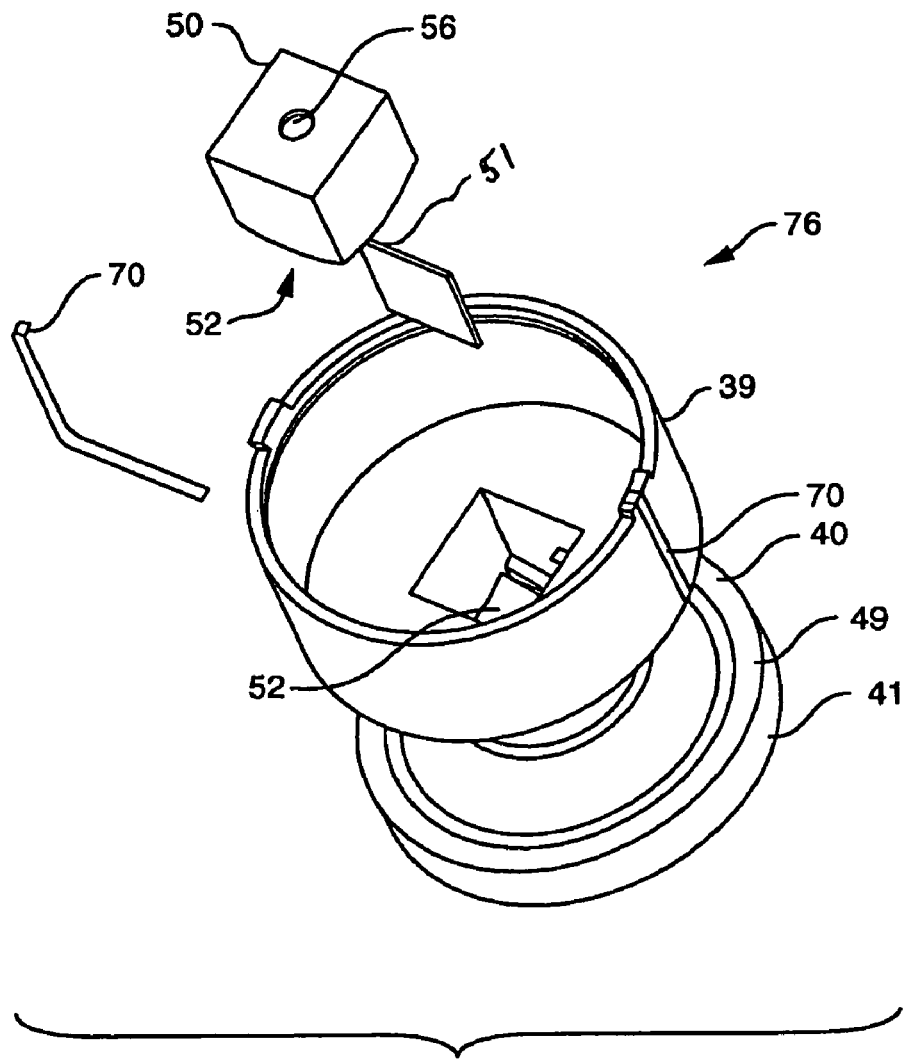
FIG. 3 is a perspective view of a portion of the hollow piston with overflow reservoir, and wherein the sensing chamber and electrode are removed to illustrate construction of the hollow piston.

In one embodiment of the invention depicted in FIG. 2A and FIG. 3, an overflow chamber (39) positioned within the hollow piston (40) adjacent the sensing chamber (50) is provided, the overflow chamber in fluid communication with the sensing chamber outlet port (56). As the sample flows into and fills the sensing chamber (50), any excess portion of the sample flows through sensing chamber opening (56) into the overflow chamber (39), thereby ensuring that there is no spillage of the sample, and minimizing the risk of contact by other persons with the sample.

FIG. 3 is a perspective view of an embodiment of the disclosed apparatus (76), with parts removed to show how it may be assembled. The center section of the hollow piston (40) is configured to enclose the sensing chamber (50), and is located between the overflow chamber (39) and the top surface (49) of the conical portion of the hollow piston (40). FIG. 3 and FIG. 2A show the opening (56) of the sensing chamber (50) to the overflow chamber (39). FIG. 2A shows a removable cap (62) to access the sensing chamber (50), and also shows a vent with filter (64) on the vented cap (24).

FIG. 2A and FIG. 3 also shows the location of sensing chamber inlet port (52) in fluid communication with the hollow piston outlet port (48). In FIG. 2A, a cross sectional view of an embodiment of the disclosed apparatus, the hollow piston outlet port (48) is shown to be at the sensing chamber inlet port (52), for fluid communication therebetween.

As shown in FIG. 2A, in one embodiment of the disclosed apparatus, the open top end (28) of the sample container (22) further comprises a first mating portion (30), and the hollow piston (40) comprises a vented cap (24).

The first mating portion (30) of the sample container (22) may include projections or grooves for a snap-together-fit, or threads for a screw-fit. The vented cap (24) has an outer surface and an inner surface (25) comprising a second mating portion (31), the inner surface (25) shaped to sealingly mate with the open top end (28) of the sample container (22). The second mating portion (31) of the vented cap (24) may include projections, grooves, or threads complementary to the first mating portion (30) of the sample container (22).

In one embodiment of the invention the first and second mating portions are independently chosen from a snap-together pair of posts and complementary slots, and a screw-fastened, inclined plane thread and complementary groove. In the embodiment shown in FIG. 2A, the hollow piston (40) snaps securely in place when fully inserted in the sample container (22).

The Sensing Chamber and a Connection to a Read-out Analyzer

In one embodiment of the disclosed apparatus shown in FIG. 3, the sensing chamber (50) is shaped to fit within the overflow chamber (39), and includes a plurality of sensing chamber electrodes (51) at the sensing chamber (50), the plurality of sensing chamber electrodes (51) configured to contact the portion of the sample contained in the sensing chamber (50). In one embodiment, the plurality of sensing chamber electrodes (51) are inserted in the wall of the sensing chamber (50).

The disclosed apparatus may further include at least one contact (70) operably connected in conductive communication with at least one of the plurality of sensing chamber electrodes (51), permitting communication of at least one of the plurality of sensing chamber electrodes (51) to a readout analyzer (20) for detection and analysis. It should be noted that any mechanical configuration that provides the ability to detect an electrical characteristic of the sample is an embodiment within the scope of the invention. Although we have implemented one form of electrical contact of the sample with the analyzer (20), there are other possible arrangements. An electrode need not be of any particular shape. We describe electrodes and separate contacts; however, the electrodes and contacts could be one and the same.

The disclosed read-out analyzer (20) may include a base (21) upon which the closed bottom end of the sample container (22) may be positioned, at least one mating contact oriented and positioned to contact the at least one contact (70) at the hollow piston outer surface or the outer surface of the vented cap (24) when the sample container (22) with the vented cap (24) mated thereon is positioned on the base (21); and the read-out analyzer (20) is in electrical contact with the at least one mating contacts (70).

When the read-out analyzer (20) is operably connected with the plurality of sensing chamber electrodes (51), application of an electrical signal to the sample is enabled. The disclosed read-out analyzer (20) is capable of detecting an electrical or a magnetic property of the sample.

For example, the embodiment depicted in FIG. 3 also includes a first pair of electrical contacts (70) at the sensing chamber electrode (51). The first pair of electrical contacts (70) may extend to an outer surface of the hollow piston (40), for example at the outer wall of the overflow chamber (39).

As shown in FIG. 2A, at least one of the first pair of electrical contacts (70) at a sensing chamber electrode (51) may also extend to an outer surface of the vented cap (24).

When the sample cup (22) containing a sample in the sensing chamber (50) is inserted into the read-out instrument or analyzer (20) in order to measure the impedance of the sample, the first pair of electrical contacts (70) on the outer surface of the vented cap (24) may operably connect the plurality of sensing chamber electrodes (51) to the internal electronics of the analyzer (20). The connection enables the application of an electrical signal from the analyzer (20) to the sample.

A Centrifugable System

Figure 4:
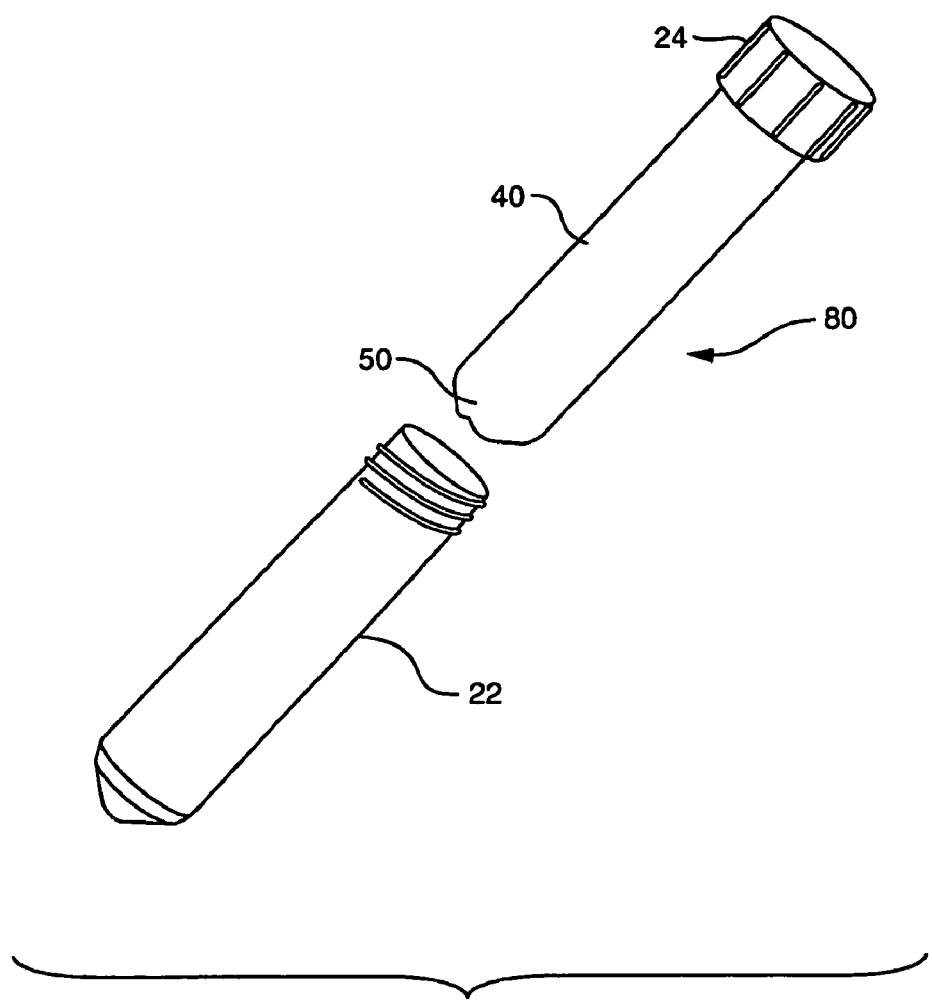
FIG. 4 is a side view of an embodiment of a sample container and piston assembly suitable for centrifuging.

FIG. 4 depicts an embodiment of the disclosed apparatus suitable for centrifuging a sample container. The device (80) includes a centrifugable sample container (22), into which may be inserted hollow piston (40) containing a sensing chamber (50) with a sensing chamber electrode (not shown). A vented cap (24) covers one open end of the hollow piston (40). An opening (not shown) in the end of the hollow piston (40) opposite the vented cap (24), allows for a sample in the sample container (22) to move into the sensing chamber (50) when the hollow piston (40) is inserted into the sample container (22).

The Syringe Type Apparatus

Figure 5:
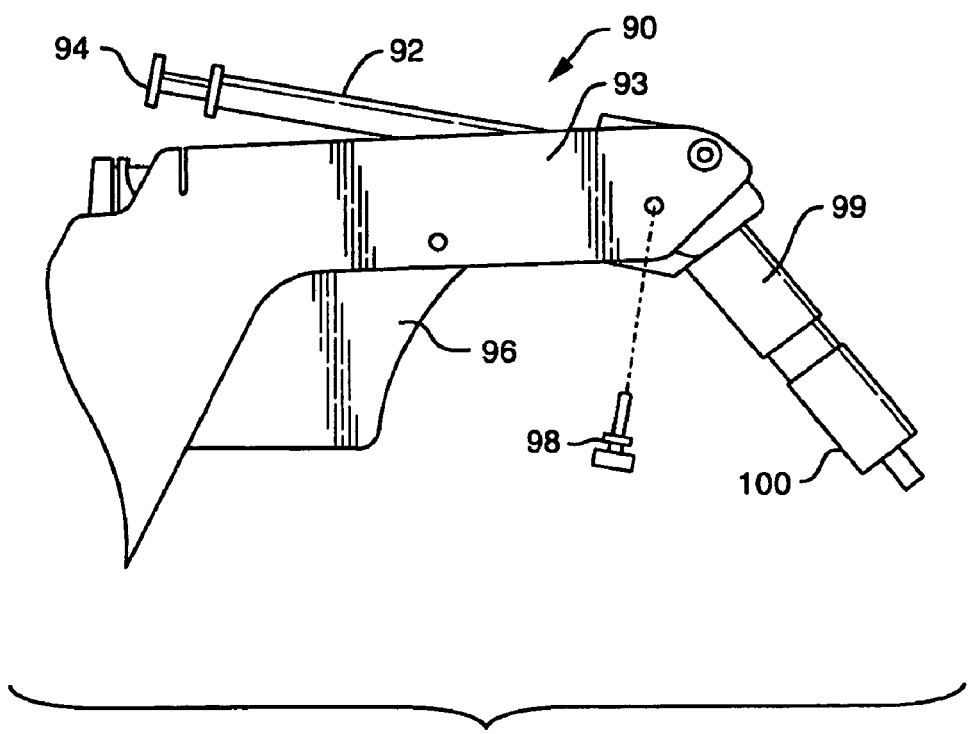
FIG. 5 is a side view of an analyzer device configured to pull a sample into the sensing chamber.

Yet another embodiment of the invention, an analyzer device configured for pulling a sample into the sensing chamber, is depicted in FIG. 5. FIG. 5 schematically depicts an apparatus (90) for collecting a sample and optionally detecting or analyzing an electrical property thereof, the apparatus comprising:

a syringe (92) mounted on a support (93), the syringe comprising a syringe plunger (94);

a trigger or lever (96) attached to the support (93) and mechanically connected to the syringe plunger (94) for drawing in or for expelling a sample;

a sensing chamber (99) comprising a plurality of sensing chamber electrodes (not shown), the sensing chamber (99) fluidly connected to a sensing head (100) and positioned between the sensing head (100) and the syringe (92), such that when the trigger or lever (96) is activated for drawing in the sample, the sample is drawn into the sensing chamber (99) and placed in contact with the plurality of sensing chamber electrodes;

a plurality of sensing chamber contacts disposed external to the sensing chamber, and operably connected in conductive communication with the sensing chamber electrodes; and a read-out analyzer (not shown) including a plurality of mating contacts configured to mate with the plurality of sensing chamber contacts, the read-out analyzer configured for detecting and analyzing a property of the sample, and the plurality of mating contacts of the read-out analyzer configured to interface with the sensing chamber contacts, thereby enabling application of an electrical signal to the sample for detection and analysis. In one embodiment the support (93) includes a set screw (98).

Method of Detecting and Analyzing and Electrical Property of a Sample

Yet another embodiment of the invention is a method of reducing a volume of a sample and optionally detecting and analyzing an electrical property of the sample, the method comprising:

directing a sample into a sensing chamber (50, 99), the sensing chamber (50, 99) comprising a plurality of sensing chamber electrodes (51) positioned within the sensing chamber (50, 99) and configured to be in contact with the sample when the sample is directed into the sensing chamber (50, 99);

applying an electrical signal to the sample with a read-out analyzer (20), via the plurality of sensing chamber electrodes (51); the plurality of sensing chamber electrodes (51) in operable communication with the read-out analyzer (20); and detecting the effect of the sample on the electrical signal, thereby determining an electrical property of the sample.

In another embodiment of the method described in the preceding paragraph, the directing includes using a piston (94) to direct the sample, or using suction to pull the sample into the sensing chamber (50, 99).

The disclosed method may include applying an electrical signal via a plurality of electrical contacts each in operable communication with each sensing chamber electrode (51) of the plurality of sensing chamber electrodes (51) respectively, the plurality of electrical contacts configured to interface with a plurality of contacts on the read-out analyzer (20). The disclosed method of determining an electrical property includes an impedance measurement.

Experimental Results

Extensive experiments were conducted successfully demonstrating the ability of the device to identify sub-standard from acceptable specimens. These data are summarized in FIG. 6 and FIG. 7.

Figure 6:
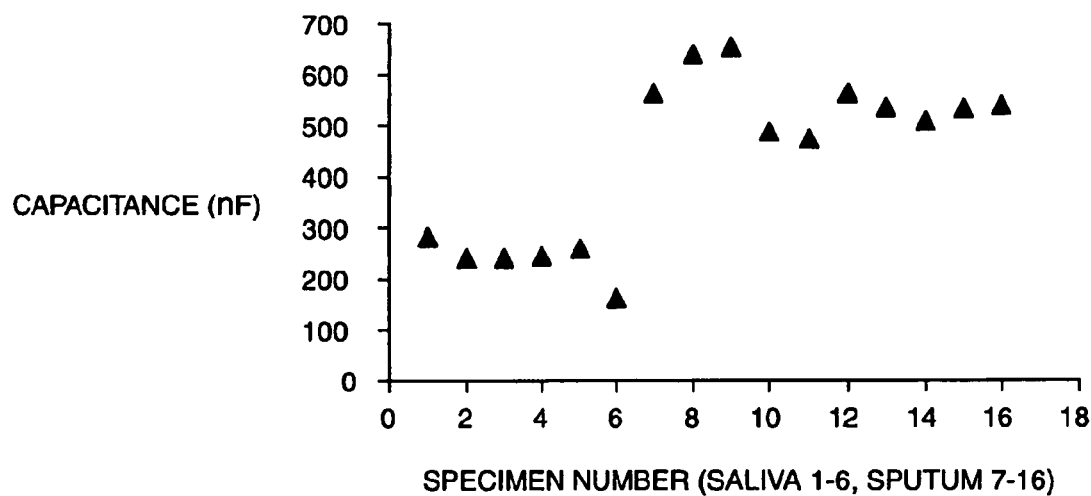
FIG. 6 is a graphical representation of capacitance measurements for each of six saliva specimens and ten sputum specimens.

FIG. 6 represents graphically the capacitance measurements (ordinate) obtained from multiple saliva and sputum specimens with the disclosed device and method. A total of six saliva specimens (Specimens 1-6) and 10 sputum specimens (Specimens 7-16) were tested. Two well-separated clusters of capacitance values are seen in FIG. 6 that correspond to the saliva and sputum specimens, respectively. Specifically, the average capacitance value for the six saliva specimens is equal to 238±41 nF; the corresponding average capacitance value for the ten sputa specimens is equal to 548±59 nF. The separation is equal to an easily recognizable difference of 310±72 nF. This separation in capacitance values demonstrates the ability to distinguish saliva from sputum specimens and consequently sub-standard from acceptable specimens.

Figure 7:
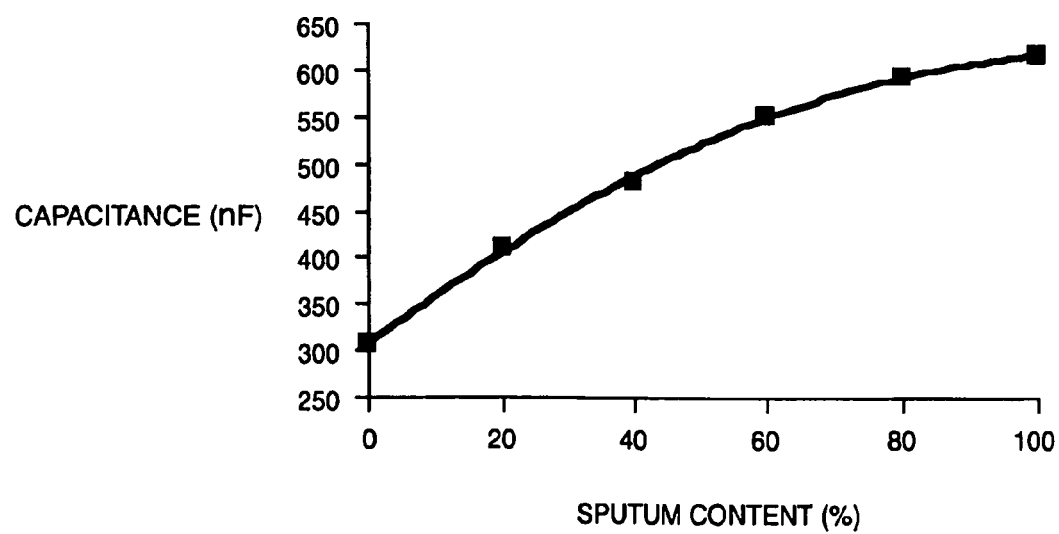
FIG. 7 is a graphical representation of capacitance measurements for each of six different concentrations of sputum diluted with saliva.

FIG. 7 is a graph of capacitance measurements of sputum diluted with saliva. The measured capacitance data points were fit to a second order polynomial curve. In FIG. 7 the capacitance measurements were from pooled sputa diluted by saliva from zero (0) percent to 100 percent by volume. These data further demonstrate the ability to determine relative amounts of sputum and saliva. A fit to these data shows a quadratic dependence of the capacitance on the sputum content. Based on this fit, the saliva/sputum ratio may be determined to better than 5 percent in a controlled experiment.

For all of these experiments, a measurement of the specimen DNA concentration (data not shown) was used as an objective measure of the diagnostic value of the specimen in addition to visual inspection. All sputa used for these experiments were judged to be "high quality" specimens.

The objective of the clinics, where the disclosed system will be used, will be to identify and replace sub-standard specimens consisting predominately of saliva with high quality specimens containing predominantly sputum. Thus, the user is interested in identifying gross inadequacies and not fine distinctions. While the system is capable of distinguishing sputum content at the level of a few percent as demonstrated by the following data, in an application of an exemplary embodiment, it is necessary only to impose a minimum threshold value for the capacitance that corresponds to a sputum content of tens of percent. This will provide the feedback to the healthcare worker needed to request an additional sample from the patient and ensure the TB specimen submitted has high diagnostic value.

This relaxed accuracy requirement enables a low-cost device suitable for wide-spread use in developing countries.

Non-Limiting Example of One Embodiment.

The analyzer (20) may be embodied as a tabletop unit. In one embodiment there is a recess in the front of the analyzer designed to precisely accept the combination of disposable sample container (22) with hollow piston (40) connected, the combination mechanically keyed to fit into the analyzer (20) in one position. When the combination container/piston is correctly fitted to the analyzer (20) the electrical contacts on the vented cap (24) make contact with the internal electronics of the analyzer (20). At the same time the electrical connection between the vented cap (24) and analyzer (20) is made, a mechanical switch within the analyzer (20) may be triggered to turn the analyzer power on and take a capacitance reading of the sample contained in the sample container (22).

In an exemplary embodiment, a single small printed circuit board containing a low-cost, low-power microprocessor-based circuit is mounted inside of the analyzer (20) shell. In one embodiment, this circuit measures the capacitance of the specimen; compares the results with a discrimination threshold determining acceptable/sub-standard specimen quality; and controls the illumination of the user-feedback LEDs. In one embodiment the circuit is be driven by DC power and configured to operate over a wide temperature range.

In one embodiment, once the cup is inserted, the electronics are activated by an external switch; the capacitance of the sample is measured, and a threshold compared, illuminating a pass/fail LED; and data logged.

In one embodiment, the analyzer (20) power is provided by a rechargable battery with the option for using A.C. power. This accommodates its use in areas where electrical power is intermittent or not available, and also enables portability for use in remote geographical areas. In one embodiment, power management uses an algorithm embedded in the microprocessor.

Although in one embodiment, the analyzer (20) presents the results to the user in the form of a red or green light, the actual capacitance values from the specimen are valuable for later analysis including setting the initial threshold and monitoring any changes along with the diagnostic health of the disclosed instrument per se. In one embodiment a non-volatile memory device such as an inexpensive memory stick may be used to record time, date, capacitance value, power level, temperature, and other relevant housekeeping data. The memory device is installed inside the analyzer (20) accessible through a panel and hidden from plain sight.

The electrodes may be constructed from a highly conductive material such as gold plated, copper-clad printed circuit board or stainless steel. The electrodes (51) may be cut from an acceptable non-reactive metal sheet stock. The contacts (70) may be stamped and formed from copper or beryllium copper. The contacts (70) do not need to be isolated because they will not be exposed to the sample fluid and thus will have a fixed capacitance.

The piston (40) may be injection molded as a single part from high density polyethylene. The sensing chamber (50) may be molded from polycarbonate. Polycarbonate allows for the higher degree of precision needed to maintain the electrode spacing.

To assemble this design, the electrodes (51) may first be inserted into the sensing chamber (50). Next, the sensing chamber (50) containing the sensing chamber electrodes (51) is inserted into the central cavity of the piston (40). Small features are molded into the piston and chamber so that all parts snap securely into place. Finally the contacts (70) would be inserted into the piston (40), making contact with each sensing chamber electrode (51).

In the embodiment shown in FIG. 3, the sensing chamber electrodes (51) are wedged into slots defining two sides of the sensing chamber (50). The connection of the sensing chamber electrodes (51) may be made using a pre-formed conducting metal strip (70) inserted through the side of the piston (40) and clipped onto the outside of the sample container (22).

The embodiment depicted in FIG. 1, FIG. 2A, and FIG. 3 is a design intended as a general clinical tool with an emphasis on smear microscopy measurements, the primary diagnostic test employed in developing countries to detect M. tb. However, in many clinics where culturing specimens is routinely performed, the specimen is collected in a standard 50 mL vial. This is desirable because the harsh reagents used as part of the standard sample preparation may be added directly into the 50 mL tube and centrifuged to obtain a pellet of mycobacteria cells for plating or growth in broth. This is in contrast to many clinics in developing countries where only raw sputum is examined.

Yet another embodiment of the invention, described above and depicted in FIG. 4 has a form factor compatible with a centrifuge tube. It may be machined from polycarbonate. This embodiment of the disclosed apparatus may include a standard 50 mL centrifuge tube (22). The assembly will consist of the 50 mL tube (22) and a hollow piston (40) fitted with a removable vented cap (24). Operation is similar to the operation of the device shown in FIG. 1-FIG. 3. A patient will expectorate into the 50 ml tube (22). Then the piston assembly (40) will be inserted into the tube (22) forcing the sample down the tube (22) and through the sample chamber at the bottom opening of the piston (40). As the cap (24) is screwed into position, the amount of sample exceeding the 1 mL sample volume is forced into the hollow area of the piston (40). The assembly is then placed in an analyzer having the same features as that shown in FIG. 1 above, but with a form factor to accommodate the elongated shape of the 50 mL tube to determine the presence of sputum. If an acceptable level of sputum is present, the sealed assembly may be sent to a laboratory and reagents may be added directly prior to the assembly being centrifuged.

In another embodiment of the invention, with no more than routine experimentation, an optical-based sensing head dedicated for absorption measurements of the bulk sample may be substituted for the impedance-based sensor component of the analyzer. Another embodiment of the invention is a kit comprising the disclosed system, a set of directions for use thereof, and other components including, for example, one or more diagnostic components for microscopy, molecular, and culture measurements.

The following literature may be useful background reading for physicians and clinical investigators. Literature Cited:
(1) "Basic Facts on TB: Stop TB, fight poverty", The Stop TB Partnership (Mar. 24, 2002).
(2) Blower S, Supervie V. "Predicting the future of XDR tuberculosis." *Lancet Infect Dis;* 7:443 (2007).
(3) Pascopella, Lisa, et al., "Laboratory Reporting of Tuberculosis Test Results and Patient Treatment Initiation in California." *J Clin Microbiol.;* 42(9): 4209-4213 (September 2004).
(4) Greenaway, C. et al., "Delay in diagnosis among hospitalized patients with active tuberculosis—predictors and outcomes." *Am. J. Respir. Crit. Care Med.* 165:927-933; (2002).
(5) Rao, V. et al., "Delays in the suspicion and treatment of tuberculosis among hospitalized patients." *Ann. Intern. Med.* 130:404-411 (1999).
(6) Sloutsky, A., et al., "Quantitative Method for Assessment of Sputum Specimen Quality in Mycobacteriology Laboratory.", presented at the ICAAC General Meeting in Toronto (1997).
(7) Alisjahbana, B, R., et al., "Better patient instruction for sputum sampling can improve microscopic tuberculosis diagnosis.", *The International Journal of Tuberculosis and Lung Disease,* 9(7): 814:817 (July 2005).

EQUIVALENTS

While this invention has been particularly shown and described with references to preferred embodiments thereof, it will be understood by those skilled in the art that various changes in form, details, and arrangement may be made therein without departing from the scope and spirit of the invention encompassed by the appended claims. With no more than routine experimentation, modifications of the disclosed apparatus may be necessary or desirable to adapt the device for a particular type of sample or test conditions. It will therefore be readily understood by those skilled in the art that the present invention is susceptible of a broad utility and application. The foregoing disclosure is not to be construed to limit the present invention or otherwise to exclude other embodiments, adaptations, variations, modifications and equivalent arrangements.

The invention claimed is:

1. An apparatus for collecting a specimen sample from a patient and optionally detecting or analyzing an electrical or magnetic property thereof, the apparatus configured to minimize the spread of infection during and subsequent to the specimen collection procedure, the apparatus comprising:

a sample container for initially receiving the specimen sample, the sample container comprising an outer surface and an inner surface, an open top end, and a closed bottom end, the closed bottom end of the sample container having a substantially convex inner surface;

a hollow piston shaped to be slidably disposed within the sample container and having a hollow piston outer surface and a hollow piston inner surface comprising a bottom portion having a substantially concave inner surface that is substantially complementary with respect to the convex inner surface of the closed bottom end of the sample container, such that when the hollow piston is lowered into the sample container, the inner surface of the hollow piston matingly engages with the inner surface of the closed bottom end of the sample container, and the hollow piston operates substantially coaxially within the sample container to sweep the specimen sample to the bottom end of the sample container, the hollow piston having a hollow piston inlet port and a hollow piston outlet port;

a sensing chamber positioned within the hollow piston, the sensing chamber having a sensing chamber inlet port in fluid communication with the hollow piston outlet port, so that as the hollow piston operates to sweep the specimen sample to the bottom end of the sample container, the specimen sample is directed out of the sample container, through the hollow piston inlet port, through the hollow piston, out the hollow piston outlet port and through the sensing chamber inlet port into the sensing chamber, thereby filling a volume within the sensing chamber with a portion of the specimen sample; and a plurality of sensing chamber electrodes at the sensing chamber, the plurality of sensing chamber electrodes configured to contact the portion of the sample contained in the sensing chamber.

2. The apparatus of claim 1 further including a read-out analyzer operably connected with the plurality of sensing chamber electrodes, thereby enabling application of an electrical signal to the specimen sample for detection and analysis.

3. The apparatus of claim 1 further including at least one contact operably connected in conductive communication with at least one of said plurality of sensing chamber electrodes permitting communication with at least one of the plurality of sensing chamber electrodes to a readout analyzer for detection and analysis.

4. The apparatus of claim 2, wherein the read-out analyzer is capable of detecting an electrical property of the specimen sample.

5. The apparatus of claim 1, wherein both the bottom portion of the hollow piston and the closed bottom end of the sample container are at least one of substantially flat, angled, conical, frustoconical, pyramidal, frustopyramidal, and hemispherical.

6. The apparatus of claim 1, wherein a bottom portion of the hollow piston comprises an external circumferential flange substantially at the bottom piston inlet port to provide increased area of contact with the inner surface of the sample container and sweep the sample off the inner surface of the sample container.

7. The apparatus of claim 1, wherein the hollow piston further comprises an overflow chamber, in fluid communication with the sensing chamber outlet port.

8. The apparatus of claim 1, wherein the open top end of the sample container further comprises a first mating portion, and wherein the hollow piston further comprises a vented cap covering the overflow chamber, the vented cap having an outer surface and an inner surface comprising a second mating portion, the inner surface shaped to sealingly mate with the open top end of the sample container.

9. The apparatus of claim 8, wherein the first and second mating portions are independently chosen from a snap-together pair of posts and complementary slots, and a screw-fasten, inclined plane thread and complementary groove.

10. The apparatus of claim 8, wherein the at least one contact at the sensing chamber electrode extends to the hollow piston outer surface or the outer surface of the vented cap.

11. The apparatus of claim 10, further comprising a read-out analyzer comprising a base upon which the closed bottom end of the sample container may be positioned, at least one mating contact oriented and positioned to contact the at least one contact at the hollow piston outer surface or the outer surface of the vented cap when the sample container with the vented cap mated thereon is positioned on the base; and the read-out analyzer in electrical contact with the at least one mating contacts.

12. The apparatus of claim 1, further comprising electrical control circuitry supporting output signaling chosen from at least one of: optical read-out capability, auditory signaling, and mechanical signaling, such output signaling used to indicate either an acceptable or a non-acceptable quality of the sample.

13. The apparatus of claim 1, wherein the sample container is a centrifugable tube.

14. The apparatus of claim 1, wherein the specimen sample comprises a fluid or a gel.

15. The apparatus of claim 2, further comprising data storage media and software to record sample readings for future analysis.

16. An apparatus for collecting a sample and optionally detecting or analyzing an electrical property thereof, the apparatus comprising:

a syringe mounted on a support, the syringe comprising a syringe plunger;
a trigger or lever attached to the support and mechanically connected to the syringe plunger for drawing in or for expelling a sample;
a sensing chamber comprising a plurality of sensing chamber electrodes, the sensing chamber fluidly connected to a sensing head and positioned between the sensing head and the syringe, such that when the trigger or lever is activated for drawing in the sample, the sample is drawn into the sensing chamber and placed in contact with the plurality of sensing chamber electrodes;
a plurality of sensing chamber contacts disposed external to the sensing chamber, and operably connected in conductive communication with the sensing chamber electrodes; and
a read-out analyzer including a plurality of mating contacts configured to mate with the plurality of sensing chamber contacts, the read-out analyzer configured for detecting and analyzing a property of the sample, and the plurality of mating contacts of the read-out analyzer configured to interface with the sensing chamber contacts, thereby enabling application of an electrical signal to the sample for detection and analysis.

17. A method of reducing a volume of a sample and optionally detecting and analyzing an electrical property of the sample, the method comprising:
directing a sample into a sensing chamber according to claim 1, the sensing chamber comprising a plurality of sensing chamber electrodes positioned within the sensing chamber and configured to be in contact with the sample when the sample is directed into the sensing chamber;
applying an electrical signal to the sample with a read-out analyzer via the plurality of sensing chamber electrodes; the plurality of sensing chamber electrodes in operable communication with the read-out analyzer; and
detecting the effect of the sample on the electrical signal, thereby determining an electrical property of the sample.

18. The method of claim 17 wherein said directing includes using a hollow piston configured to claim 1 to direct the sample into the sensing chamber.

19. The method of claim 17 wherein said applying an electrical signal is via a plurality of electrical contacts each in operable communication with each sensing chamber electrode of the plurality of sensing chamber electrodes respectively, the plurality of electrical contacts configured to interface with a plurality of contacts on the read-out analyzer.

20. The method of claim 17 wherein the determining an electrical property includes an impedance measurement.

* * * * *